United States Patent
Simonsen et al.

(10) Patent No.: US 7,425,528 B2
(45) Date of Patent: Sep. 16, 2008

(54) STABILIZATION OF GRANULES

(75) Inventors: Ole Simonsen, Soborg (DK); Erik Kjaer Markussen, Vaerlose (DK); Hanne Rojel, Havdrup (DK); Svend Kaasgaard, Soborg (DK); Thomas Honger Callisen, Frederiksberg C (DK); Christian Isak Jorgensen, Bagsvaerd (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 10/611,795

(22) Filed: Jun. 30, 2003

(65) Prior Publication Data

US 2004/0033927 A1    Feb. 19, 2004

Related U.S. Application Data

(60) Provisional application No. 60/399,824, filed on Jul. 31, 2002.

(30) Foreign Application Priority Data

Jul. 1, 2002    (DK) ............................. 2002 01023

(51) Int. Cl.
| | |
|---|---|
| C11D 3/37 | (2006.01) |
| C11D 3/386 | (2006.01) |
| C11D 7/10 | (2006.01) |
| C11D 11/02 | (2006.01) |
| C11D 17/00 | (2006.01) |
| A61K 9/16 | (2006.01) |
| A61K 9/50 | (2006.01) |

(52) U.S. Cl. .................. 510/349; 510/300; 510/361; 510/392; 510/438; 510/441; 510/446; 510/475; 510/530; 424/408; 424/418; 424/486; 424/497

(58) Field of Classification Search ............... 510/300, 510/349, 361, 392, 438, 441, 446, 475, 530; 424/408, 418, 488, 497
See application file for complete search history.

(56) References Cited

U.S. PATENT DOCUMENTS

| 5,254,287 A | 10/1993 | Deleeuw et al. |
| 5,739,091 A | 4/1998 | Kiesser et al. |
| 5,858,952 A * | 1/1999 | Izawa et al. .................. 510/392 |
| 5,972,669 A | 10/1999 | Harz et al. |
| 6,268,329 B1 | 7/2001 | Markussen |
| 7,070,820 B2 * | 7/2006 | Simonsen et al. ............. 426/96 |
| 2001/0044403 A1 | 11/2001 | Markussen |
| 2003/0073604 A1* | 4/2003 | McGoff et al. ............... 510/441 |
| 2004/0033927 A1* | 2/2004 | Simonsen et al. ........... 510/445 |

FOREIGN PATENT DOCUMENTS

| EP | 206418 | | 12/1986 |
| EP | 320129 | | 6/1989 |
| EP | WO 99/37746 | * | 7/1999 |
| WO | WO 91/17235 | | 11/1991 |
| WO | WO 00/01793 | | 1/2000 |
| WO | WO 2004/003188 | * | 1/2004 |

OTHER PUBLICATIONS

Gaertner et al., "Development of Low Dust Enzyme Detergent", Proceed. Int'l Symp. Control Rd. Bloact. Mater. Con Inc., vol. 25, p. 289-290 (1998), no month given.

* cited by examiner

Primary Examiner—Brian P Mruk
(74) Attorney, Agent, or Firm—Michael W. Krenicky

(57) ABSTRACT

The present invention relates to granules comprising a core matrix and one or more coatings, wherein the core matrix comprises: An active compound, a synthetic polymer, where the amount of polymer added is 0.1 to 10% by weight of the matrix and one or more antioxidants and/or reducing agents, where the amount of antioxidant and/or reducing agent is 0.2 to 5% by weight of the matrix.

32 Claims, No Drawings

STABILIZATION OF GRANULES

CROSS-REFERENCE TO RELATED APPLICATIONS

This application claims priority under 35 U.S.C. 119 of Danish application PA 2002 01023 filed Jul. 1, 2002 and the benefit of U.S. Provisional application No. 60/399,824, filed Jul. 31, 2002, the contents of which are fully incorporated herein by reference.

FIELD OF THE INVENTION

The present invention relates to stabilization of granules comprising an active compound e.g. an enzyme by the addition of a synthetic polymer and an antioxidant or reducing agent. The invention further relates to the manufacture of said granules and the use of them.

BACKGROUND OF THE INVENTION

It is known to the art to incorporate active compounds into dry solid particles or granules and thereby protect the active compound from inactivation and/or protect the environment from the active compound. It is further known to the art to incorporate stabilizers into the active containing particle to protect the active compound against inactivation caused by aggressive materials in the environment.

Known prior art related to stabilization of active compounds in dry granules includes U.S. Pat. No. 5,858,952, which discloses an enzyme-containing granulated product comprising an enzyme and one or more stabilizers selected from the group consisting of reducing agents and antioxidants.

U.S. Pat. No. 5,972,669 discloses methods to improve the processing and storage stability of dry enzyme preparations. To this extend an inorganic salt, e.g. $MgSO_4$, is dissolved in an enzyme containing solution which is subsequently dried, using e.g. spray drying.

WO 91/17235 discloses granules containing enzymes and an enzyme protecting agent.

SUMMARY OF THE INVENTION

There are several reasons for formulating active compounds into particles, such as preparing enzyme granules, including protection of the active compound by separating it from the surrounding potentially hostile environment until the moment when the active compound is to be used in an application.

Especially for granules comprising enzymes, hostile bleaching components in detergents can give rise to stability problems. High humidity in the surrounding environment is another parameter which can give stability problems for enzyme containing granules.

To obtain a granule, which contains an active compound, such as an enzyme, which is stable both at high humidity, at low humidity, in combination with hostile components and without hostile components, is not an easy task.

We have in our search for improved enzyme granules surprisingly found that the combination of a synthetic polymer e.g. PVP and antioxidants or reducing agents, e.g. sodium thio sulfate, provides stabilization of the active compound in all above mentioned hostile environments, when mixed in a matrix in specified amounts and result in significantly improved stability of the active compounds in the granules.

One object of the invention is to improve solid formulations for active compounds with respect to stability of the active compound. In our search for such improved formulations we have also found that by adding polysaccharides e.g. starch to the above mentioned stabilized active compound containing matrix it further improves the stability of the granule.

Hence the present invention provides in a first aspect a granule comprising a core matrix and one or more coatings, wherein the core matrix comprises:
1. An active compound.
2. A synthetic polymer, where the amount of the polymer added is 0.1 to 10% by weight of the core matrix.
3. One or more components selected from the group of antioxidants and reducing agents, where the amount of antioxidant and reducing agent is 0.2 to 5% by weight of the core matrix.

The core matrix may further comprise a polysaccharide, where the amount of polysaccharide is above 2% by weight of the matrix.

The invention also provides methods for preparation of the granules and compositions comprising the granules.

DETAILED DESCRIPTION OF THE INVENTION

The stability of active compounds comprised in granules is influenced by the surrounding environment upon storage, being chemical or physical factors decreasing the stability. In detergent formulations some detergent formulating agents such as bleaching agents destroy the activity of active ingredients such as enzymes.

Humidity is also an important factor with regard to stability of granules comprising active compounds such as enzyme granules; especially high humidity affects the stability negatively.

Hitherto, no granule comprising an active compound has been reported, wherein the active compound is stable at both high humidity and low humidity and in both environments including and excluding hostile compounds, such as bleaching agents.

We have surprisingly found that a core matrix comprising an active compound, a synthetic polymer and an antioxidant or reducing agent in specified amounts is found to improve the stability of the active compound significantly, improving the stability both at high and low humidity and in environments with and without hostile compounds, such as bleaching agents.

Synthetic polymers such as PVP are found to improve the stability of active compound containing granules, e.g. enzyme granules, especially in high humidity non hostile environment e.g. non-bleaching environments. Reducing agents or antioxidants such as Sodium thiosulfate is found to improve stability of active compound containing granules, e.g. enzyme containing granules, especially in the presence of hostile compounds such as bleaching agents and in low humidity environment.

Hence by mixing the active compound in a matrix together with a synthetic polymer such as PVP and a reducing agent or an antioxidant such as sodium thio sulfate it is possible to prepare an active compound in which the stability of the active compound is significantly improved, even in some of the most hostile environments. By this combination of granule ingredients the range of different environments in which the active compound in the granule of the invention is stablized is significantly broadened.

We have further found that polysaccharides improve the stability of active compound in all combinations of hostile/non-hostile and low humidity/high humidity environments.

It has further been found that by adding $MgSO_4$ to the above mentioned core matrix it further improves the stability of the active compound.

A further improvement we found of the granules of the invention is coating of the granules with a salt layer, it is contemplated that the salt layer prolongs the lifetime of the antioxidants or reducing agents in the core matrix even if the salt layer is very thin.

The granule of the present invention comprises an enzyme core matrix, one or more coatings wherein these coatings optionally may be a salt coating and a protective coating.

Definitions

The term "% RH" is used throughout the text, and in context of the invention the term is to be understood as the relative humidity of air. 100% RH is air saturated with water moisture at a fixed temperature and % RH thus reflects the percent moisture saturation of the air.

By high humidity is meant humidity higher than 65% RH.
By low humidity is meant humidity below 65% RH.

The term "matrix" is to be understood as the mixture which comprises the active compound. The "core matrix" either makes up the entire homogenous core of the granule or makes up the mixture which is applied to a preformed inert core.

The Core

The core matrix of the invention comprises:
a. An active compound.
b. A synthetic polymer, where the amount of polymer added is 0.1 to 10% by weight of the core matrix.
c. One or more components selected from the group of antioxidants and reducing agents, where the amount of antioxidant and reducing agent is 0.2 to 5% by weight of the core matrix.

In a particular embodiment of the present invention the matrix further comprises a polysaccharide, where the amount of polysaccharide is above 2% by weight of the matrix.

Active Compounds

The active compound of the invention may be any active component or mixture of active components, which benefits from being separated from the environment surrounding the granule. The term "active" is meant to encompass all compounds, which upon release from the granule upon applying the granule of the invention in a process serve a purpose of improving the process. Suitable active compounds are those, which are either subject of deactivation and/or causing deactivation to other components in the compositions of the invention. The active compound may be present dispersed as discrete solid particles in the core matrix.

The active compound may be inorganic of nature or organic of nature. Particularly active compounds are active biological compounds which are usually very sensitive to the surrounding environment such as compounds obtainable from microorganisms. More particularly active compounds are peptides or polypeptides or proteins. Most particularly active compounds are proteins such as enzymes.

The enzyme in the context of the present invention may be any enzyme or combination of different enzymes. Accordingly, when reference is made to "an enzyme" this will in general be understood to include combinations of one or more enzymes.

It is to be understood that enzyme variants (produced, for example, by recombinant techniques) are included within the meaning of the term "enzyme". Examples of such enzyme variants are disclosed, e.g. in EP 251,446 (Genencor), WO 91/00345 (Novo Nordisk), EP 525,610 (Solvay) and WO 94/02618 (Gist-Brocades Nev.).

The enzyme classification employed in the present specification with claims is in accordance with *Recommendations (1992) of the Nomenclature Committee of the International Union of Biochemistry and Molecular Biology*, Academic Press, Inc., 1992.

Accordingly the types of enzymes which may appropriately be incorporated in granules of the invention include oxidoreductases (EC 1. - . - . - ), transferases (EC 2. - . - . - ), hydrolases (EC 3. - . - . - ), lyases (EC 4. - . - . - ), isomerases (EC 5. - . - . - ) and ligases (EC 6. - . - . - ).

Preferred oxidoreductases in the context of the invention are peroxidases (EC 1.11.1), *laccases* (EC 1.10.3.2) *and glucose oxidases* (EC 1.1.3.4)]. An Example of a commercially available oxidoreductase (EC 1.-.-.-) is Gluzyme™ (enzyme available from Novozymes A/S). Further oxidoreductases are available from other suppliers. Preferred transferases are transferases in any of the following sub-classes:

a) Transferases transferring one-carbon groups (EC 2.1);

b) transferases transferring aldehyde or ketone residues (EC 2.2); acyltransferases (EC 2.3);

c) glycosyltransferases (EC 2.4);

d) transferases transferring alkyl or aryl groups, other that methyl groups (EC 2.5); and e) transferases transferring nitrogeneous groups (EC 2.6).

A most preferred type of transferase in the context of the invention is a transglutaminase (protein-glutamine γ-glutamyltransferase; EC 2.3.2.13).

Further examples of suitable transglutaminases are described in WO 96/06931 (Novo Nordisk A/S).

Preferred hydrolases in the context of the invention are: carboxylic ester hydrolases (EC 3.1.1.-) such as lipases (EC 3.1.1.3); phytases (EC 3.1.3.-), e.g. 3-phytases (EC 3.1.3.8) and 6-phytases (EC 3.1.3.26); glycosidases (EC 3.2, which fall within a group denoted herein as "carbohydrases"), such as α-amylases (EC 3.2.1.1); peptidases (EC 3.4, also known as proteases); and other carbonyl hydrolases.

In the present context, the term "carbohydrase" is used to denote not only enzymes capable of breaking down carbohydrate chains (e.g. starches or cellulose) of especially five- and six-membered ring structures (i.e. glycosidases, EC 3.2), but also enzymes capable of isomerizing carbohydrates, e.g. six-membered ring structures such as D-glucose to five-membered ring structures such as D-fructose.

Carbohydrases of relevance include the following (EC numbers in parentheses): α-amylases (EC 3.2.1.1), β-amylases (EC 3.2.1.2), glucan 1,4-α-glucosidases (EC 3.2.1.3), endo-1,4-beta-glucanase (cellulases, EC 3.2.1.4), endo-1,3 (4)-β-glucanases (EC 3.2.1.6), endo-1,4-β-xylanases (EC 3.2.1.8), dextranases (EC 3.2.1.11), chitinases (EC 3.2.1.14), polygalactu-ronases (EC 3.2.1.15), lysozymes (EC 3.2.1.17), β-glucosidases (EC 3.2.1.21), α-galactosidases (EC 3.2.1.22), α-galactosidases (EC 3.2.1.23), amylo-1,6-glucosidases (EC 3.2.1.33), xylan 1,4-β-xylosidases (EC 3.2.1.37), glucan endo-1,3-β-D-glucosidases (EC 3.2.1.39), α-dextrin endo-1,6-α-glucosidases (EC3.2.1.41), sucrose α-glucosidases (EC 3.2.1.48), glucan endo-1,3-α-glucosidases (EC 3.2.1.59), glucan 1,4-α-glucosidases (EC 3.2.1.74), glucan endo-1,6-β-glucosidases (EC 3.2.1.75), arabinan endo-1,5-α-L-arabinosidases (EC 3.2.1.99), lactases (EC 3.2.1.108), chitosanases (EC 3.2.1.132) and xylose isomerases (EC 5.3.1.5).

Examples of commercially available proteases (peptidases) include Kannase™, Everlase™, Esperase™, Alcalase™, Neutrase™, Durazym™, Savinase™, Pyrase™, Pancreatic Trypsin NOVO (PTN), Bio-Feed™ Pro and Clear-Lens™ Pro (all available from Novozymes A/S, Bagsvaerd, Denmark).

Other commercially available proteases include Maxatase™, Maxacal™, Maxapem™, Opticlean™ and Purafect™ (available from Genencor International Inc. or Gist-Brocades).

Examples of commercially available lipases include Lipoprime™ Lipolase™, Lipolase™ Ultra, Lipozyme™, Palatase™, Novozy™ 435 and Lecitase™ (all available from Novozymes A/S).

Other commercially available lipases include Lumafast™ (Pseudomonas mendocina lipase from Genencor International Inc.); Lipomax™(Ps. pseudoalcaligenes lipase from Gist-Brocades/Genencor Int. Inc.; and Bacillus sp. lipase from Solvay enzymes. Further lipases are available from other suppliers.

Examples of commercially available carbohydrases include Alpha-Gal™, Bio-Feed™ Alpha, Bio-Feed™Beta, Bio-Feed™Plus, Bio-Feed™Plus, Novozyme™ 188, Celluclast™ Cellusoft™, Ceremyl™, Citrozym™, Denimax™, Dezyme™, Dextrozyme™, Finizym™, Fungamyl™, Gamanase™, Glucanexm, Lactozym™, Maltogenase™, Pentopan™, Pectinex™, Promozyme™, Pulpzyme™, Novamyl™, Termamyl™, AMG™ (Amyloglucosidase Novo), Maltogenase™, Sweetzyme™ and Aquazy™ (all available from Novozymes A/S). Further carbohydrases are available from other suppliers.

Synthetic Polymers

By synthetic polymers is meant polymers which backbone has been polymerised synthetically.

Suitable synthetic polymers of the invention includes in particular polyvinyl pyrrolidone (PVP), polyvinyl alcohol (PVA), polyvinyl acetate, polyacrylate, polymethacrylate, poly-acrylamide, polysulfonate, polycarboxylate, and copolymers thereof, in particular water soluble polymers or copolymers.

In a particular embodiment of the present invention the synthetic polymer is a vinyl polymer.

In a preferred embodiment of the present invention the synthetic polymer is PVP or a copolymer thereof e.g. a PVP/vinyl acetate copolymer.

Where polyvinyl pyrrolidone is used we prefer to use a polymer with a molecular weight of 1,000 g/mol to 1,500,000 g/mol. For good stabilization we prefer molecular weights below 1,000,000 g/mol e.g. below 800,000 g/mol, especially below 200,000 g/mol and most preferably below 100,000 g/mol. We generally prefer to use molecular weights above 5,000 g/mol, especially above 10,000 g/mol, more particularly above 20,000 g/mol, e.g. above 25,000 g/mol.

The amount of synthetic polymer used in the matrix of the present invention is particularly 0.1 to 10%, more particularly 0.2 to 5% by weight, even more particularly 0.5 to 3% by weight, most particularly 1 to 2.5% by weight.

Some synthetic polymers do have hygroscopic properties which will result in a negative effect on the stability of the granules if the amount used in the matrix is too high, and if large amounts of synthetic polymer are added the process conditions are affected in a negative way as the viscosity will become too high. If the amount of synthetic polymer is too small the stabilization effect is not seen. Furthermore synthetic polymers are expensive compared to other granulation materials so it is wishful to keep the amount necessary as low as possible. In view of these arguments the amount of synthetic polymer added to the matrix is a balance to reach an optimum of stabilization.

Antioxidants and Reducing Agents

Examples of suitable antioxidants and reducing agents of the present invention are salts of alkali metals and earth alkali metals, salts of sulfite, thiosulfite, thiosulfate, erythorbate, citrate, isopropyl citrate and ascorbate or corresponding acids, silicates, carbonates or bicarbonates, phosphates and nitrite, other suitable materials are methionine, glycine, propyl gallate, tertbutyl hydroquinone, tocopherols, thiodipropionic acid, butylated hydroxytoluene (BHT), butylated hydroxyanisol (BHA) or tannic acid. In particular salts of thiosulfates, e.g. sodium thiosulfate, are suitable. The amount of antioxidant or reducing agent used in the matrix of the present invention is particularly 0.2 to 5% by weight, more particularly 0.5 to 4% by weight, even more particular 1 to 3% by weight, most particular 1 to 2% by weight of the matrix.

Below 0.2% by weight of the core matrix no significant stabilization effect is seen and above 5% added antioxidant or reducing agent the stabilization effect may be influenced in a negative way by several things; some of the antioxidants and/or reducing agents have hygroscopic properties which gives a negative effect in high humidity environments. Furthermore some salts do have an unpleasant odour and when used in too high amounts the smell will influence negatively on the final product. Even further when making the granules the preparation of the core matrix may include mixing the synthetic polymer and the antioxidant and/or reducing agent together with a liquid, e.g. enzyme concentrates, to get the two compounds in a dissolved form to achieve a more homogenous mixture in the core matrix. In some cases it is seen that if the amount of antioxidant or reducing agent becomes too high the synthetic polymer precipitates.

If the antioxidant or reducing agent is added to a liquid, e.g. comprising an enzyme, during preparation the solubility of the antioxidant or reducing agent can be another limiting factor.

Polysaccharides

The polysaccharides of the present invention may be unmodified naturally occurring polysaccharides or modified naturally occurring polysaccharides.

Suitable polysaccharides include cellulose, pectin, dextrin and starch. The starches may be soluble or insoluble in water.

In a particular embodiment of the present invention the polysaccharide is a starch. In a particular embodiment of the present invention the polysaccharide is an insoluble starch.

Naturally occurring starches from a wide variety of plant sources are suitable in the context of the invention (either as starches per se, or as the starting point for modified starches), and relevant starches include starch from: rice, corn, wheat, potato, oat, cassava, sago-palm, yuca, barley, sweet potato, sorghum, yams, rye, millet, buckwheat, arrowroot, taro, tannia, and may for example be in the form of flour.

Cassava starch is among preferred starches in the context of the invention; in this connection it may be mentioned that cassava and cassava starch are known under various synonyms, including tapioca, manioc, mandioca and manihot.

As employed in the context of the present invention, the term "modified starch" denotes a naturally occurring starch, which has undergone some kind of at least partial chemical modification, enzymatic modification, and/or physical or physicochemical modification, and which—in general—exhibits altered properties relative to the "parent" starch.

The amount of polysaccharides used in the matrix of the present invention is particularly above 2% by weight, more particular 2 to 75% by weight, even more particularly 2 to 50% by weight, even more particularly 5 to 30% by weight and most particularly 10 to 20% by weight of the matrix.

Too high amounts of polysaccharides may result in porous granules which give a negative affect on rigidity of the granule and by that a negative effect on dust figures.

The amount of starch used in the matrix of the present invention is particular above 2% by weight of the matrix, more particular above 5% by weight.

The amount of starch used in the matrix of the present invention is particular 2 to 30% by weight of the matrix, more particular above 2 to 20% by weight, most particular 5 to 15% by weight.

We have found that as an alternative to or a supplement to adding synthetic polymers or polysaccharides to the matrix other promising candidates which have similar stabilizing effect are in-active proteins such as casein, albumin and gelatin and protein sources coming from potato, rice, corn, corn steep liquor, wheat, soy.

Addition of polysaccharides and/or proteins to the matrix may be in the form of enzyme fermentation broth and/or enzyme recovery sludge, but enzyme fermentation broth and/or enzyme recovery sludge may also be added besides polysaccharides and/or proteins. Enzyme fermentation broth and enzyme recovery sludge is typically the residues from fermentation step of enzymes and following recovery step of enzymes respectively. In a particular embodiment of the present invention the core matrix comprises an in-active protein, which may be added in the form of enzyme fermentation broth and/or recovery sludge.

In a preferred embodiment of the present invention the core matrix comprises:
 a. An active compound.
 b. A synthetic polymer, where the amount of polymer added is 0.1 to 10% by weight of the matrix.
 c. One or more antioxidants and/or reducing agents, where the amount of antioxidant and/or reducing agent is 0.2 to 5% by weight of the matrix.
 d. A polysaccharide, where the amount of polysaccharide is above 2% by weight of the matrix In a particular embodiment of the present invention the synthetic polymer is PVP, the antioxidant is sodium thiosulfate and the polysaccharide is starch We have further found that by adding a soluble inorganic salt to the matrix of the present invention the active compound containing granules become more stable.

Inorganic Salts:

The matrix may further comprise a soluble inorganic salt, wherein said inorganic salt comprises a divalent cation selected from the group of zinc, magnesium and calcium, in particular Magnesium sulfate and zinc sulfate. Divalent cations are preferred because they provide the best storage and processing stability. Sulfate is preferred as anion because it provides the best drying yield. In a particular embodiment of the present invention the salt is magnesium sulfate.

Salts mentioned in the section "Coatings" (below) may also be used.

The amount of salt used in the matrix of the present invention is particularly 1 to 70% by weight, more particularly 2 to 30% by weight more particularly 2 to 10% by weight.

Auxiliary Matrix Components:

The matrix may further comprise known conventional core material as auxiliary matrix components such as binders, solvents, fillers etc. these are described in WO 89/08694, WO 89/08695, EP 270608 B1 and/or WO 00/01793. Other examples of conventional coating materials may be found in U.S. Pat. No. 4,106,991, EP 170360, EP 304332, EP 304331, EP 458849, EP 458845, WO 97/39116, WO 92/12645A, WO 87/07292, WO 91/06638, WO 92/13030, WO 93/07260, WO 93/07263, WO 96/38527, WO 96/16151, WO 97/23606, U.S. Pat. No. 5,324,649, U.S. Pat. No. 4,689,297, EP 206417, EP 193829, DE 4344215, DE 4322229 A, DD 263790, JP 61162185 A and/or JP 58179492. Other enzyme stabilizers used may be boric acid and sodium tetraborate.

In a particular embodiment of the present invention, the core matrix of the present invention is used together with the concept of WO 01/25412, which is hereby incorporated by reference.

The core matrix may optionally be coated onto a preformed core.

Preformed Cores

Preformed cores also called carrier nuclei, placebo nuclei (nucleus free of active compound) or seeds are inert particles upon which the mixture comprising the active compound can be layered. The preformed cores may comprise inorganic salts, sugars, sugar alcohols, small organic molecules such as organic acids or salts, minerals such as clays or silicates or a combination of two or more of these.

In a particular embodiment of the present invention the core may be prepared by applying the mixture comprising the active compound onto a preformed core.

Coatings

The granule may comprise one or more coatings. The coatings may be from 1 □ to 1500 □ thick. In a particular embodiment the coating is more than 30 □ thick, in a more particular embodiment the coating is more than 50 □ thick, in a most particular embodiment the coating is more than 75 □ thick. In a particular embodiment the coating is less than 1000 □ thick, in a more particular embodiment the coating is less than 500 □ thick, in an even more particular embodiment the coating is less than 250 □ thick, in a most particular embodiment the coating is less than 150 □ thick.

We have surprisingly found that by applying even a thin salt coating the stability of the granules increases, by adding a salt coating the lifetime of the antioxidant is prolonged. In a particular embodiment the granules comprise a thin salt coating.

Salt Coating

A salt coating which is 2 to 5 □ thick shows a significant improvement in stability. In a particular embodiment of the present invention the salt coating comprise 2 to 30% by weight of the matrix and the salt coating. In a more particular embodiment the amount of salt is 3 to 10% by weight of the matrix and the salt coating.

The salt coating may for other reasons than stability be a thick coating such as protection and integrity.

In a particular embodiment of the present invention the thickness of the salt coating is 1 □ to 1000 □ thick. In a more particular embodiment of the present invention the salt coating is 2 □ to 100 □ thick. In an even more particular embodiment of the present invention the salt coating is 3 □ to 20 □ thick.

In a particular embodiment the salt coating is less than 500 □ thick. In a more particular embodiment the salt coating is less than 250 □ thick. In an even more particular embodiment of the present invention the salt coating is less than 100 □ thick. In an even more particular embodiment of the present invention the salt coating is less than 80 □ thick. In a more particular embodiment of the present invention the salt coating is less than 50 □ thick. In a most particular embodiment the salt coating is less than 30 □ thick.

The salt coating comprises one or more salts. The salt may be an inorganic salt, e.g. salts of sulfate, sulfite, phosphate, phosphonate, nitrate, chloride or carbonate or salts of simple organic acids (less than 10 carbon atoms e.g. 6 or less carbon atoms) such as citrate, malonate or acetate. Examples of cations in these salt are alkali or earth alkali metal ions, although the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, lactate, formate, acetate, butyrate, propionate, benzoate, tartrate, ascorbate or gluconate. In particular alkali- or earth alkali metal salts of sulfate, sulfite, phosphate, phosphonate, nitrate, chloride or carbonate or salts of simple organic acids such as citrate, malonate or acetate may be used. Specific examples include $Na_2HPO_4$, $Na_3PO_4$, $(NH_4)H_2PO_4$, $KH_2PO_4$, $Na_2SO_4$, $K_2SO_4$, $KHSO_4$, $ZnSO_4$, $MgSO_4$, $CuSO_4$, $Mg(NO_3)_2$, $(NH_4)_2SO_4$, sodium borate, magnesium acetate and sodium citrate.

The salt may also be a hydrated salt, i.e. a crystalline salt hydrate with bound water(s) of crystallization, such as described in WO 99/32595. Examples of hydrated salts include magnesium sulfate heptahydrate ($MgSO_4(7H_2O)$), zinc sulfate heptahydrate ($ZnSO_4(7H_2O)$), copper sulfate pentahydrate ($CuSO_4(5H_2O)$), sodium phosphate dibasic heptahydrate ($Na_2HPO_4(7H_2O)$), magnesium nitrate hexahydrate ($Mg(NO_3)_2(6H_2O)$), sodium borate decahydrate, sodium citrate dihydrate and magnesium acetate tetrahydrate.

Additional Coatings

The granule comprising the matrix and optionally a salt coating may further be coated with one or more coating layers to provide further improved properties of the granule. Conventional coatings and methods as known to the art may suitably be used, such as the coatings described in WO 89/08694, WO 89/08695, 270 608 B1 and/or WO 00/01793. Other examples of conventional coating materials may be found in U.S. Pat. No. 4,106,991, EP 170360, EP 304332, EP 304331, EP 458849, EP 458845, WO 97/39116, WO 92/12645A, WO 89/08695, WO 89/08694, WO 87/07292, WO 91/06638, WO 92/13030, WO 93/07260, WO 93/07263, WO 96/38527, WO 96/16151, WO 97/23606, U.S. Pat. No. 5,324,649, U.S. Pat. No. 4,689,297, EP 206417, EP 193829, DE 4344215, DE 4322229 A, DD 263790, JP 61162185 A and/or JP 58179492.

The coating may comprise materials selected from binders, fibers, salts, water insoluble minerals, pigments, dyes, enzyme stabilizers or combinations thereof and any granulation materials mentioned above in the section "The core".

Hostile Compounds

In the present invention hostile compounds are compounds which are found to decrease the activity of the active compound. Examples of hostile compounds can be but are not limited to bleaching agents, alkaline components, anionic surfactants, metal complexing agents (e.g. builders).

Preparation of the Granule

The invention further encompasses a process for preparing the granules, wherein the granule comprises a core matrix and one or more coatings, wherein the core matrix comprises:
 a. An active compound.
 b. A synthetic polymer, where the amount of polymer added is 0.1 to 10% by weight of the core matrix.
 c. One or more components selected from the group of antioxidants and reducing agents, where the amount of antioxidant and reducing agent is 0.2 to 5% by weight of the core matrix.

The granules may be prepared by methods known to those skilled in the art of enzyme granulation, including mixer granulation, fluid bed coating, prilling, disc granulation, pan drum coating, spray drying, extrusion, fluid bed spray drying, high shear agglomeration, spheronization or combinations of these techniques.

Preparation of the Core Matrix

Methods for preparing the core matrix particles include known enzyme granule formulation technologies e.g. spray drying, fluid bed, fluid bed spray drying, mixer granulation, pan drum process and extrusion. Other relevant core particles are layered products, absorbed products, pelletized products, prilled products. The cores may optionally be dried after granulation.

The following enzyme granules formulation technologies may be used in preparation of the granules:

Spray dried products may be prepared by a liquid enzyme-containing solution which is atomised in a spray drying tower to form small droplets which during their way down the drying tower dry to form an enzyme-containing particulate material. Very small particles can be produced this way (Michael S. Showell (editor); Powdered detergents; Surfactant Science Series; 1998; vol. 71; page 140-142; Marcel Dekker).

Layered products includes products where enzyme is coated as a layer around a preformed inert core particle, wherein an enzyme-containing solution is atomised, typically in a fluid bed apparatus wherein the pre-formed core particles are fluidised, and the enzyme-containing solution adheres to the core particles and dries up to leave a layer of dry enzyme on the surface of the core particle. Particles of a desired size can be obtained this way if a useful core particle of the desired size can be found. This type of product is described in e.g. WO 97/23606.

During preparation of absorbed core particles, the enzyme is absorbed onto and/or into the surface of the core, rather than coating the enzyme as a layer around the core. Such a process is described in WO 97/39116.

Extrusion or pelletized products may be prepared by an enzyme-containing paste is pressed to pellets or under pressure is extruded through a small opening and cut into particles which are subsequently dried. Such particles usually have a considerable size because of the material in which the extrusion opening is made (usually a plate with bore holes) sets a limit on the allowable pressure drop over the extrusion opening. Also, very high extrusion pressures when using a small opening increase heat generation in the enzyme paste, which is harmful to the enzyme. (Michael S. Showell (editor); Powdered detergents; Surfactant Science Series; 1998; vol. 71; page 140-142; Marcel Dekker). In a particular embodiment of the present invention the synthetic polymer and/or the polysaccharide and/or the protein source and/or the antioxidants are mixed together with a liquid e.g. enzyme concentrate or fermentation broth and then extruded.

Prilled products, includes products where an enzyme powder is suspended in molten wax and the suspension is sprayed, e.g. through a rotating disk atomiser, into a cooling chamber where the droplets quickly solidify (Michael S. Showell (editor); Powdered detergents; Surfactant Science Series; 1998; vol. 71; page 140-142; Marcel Dekker). The product obtained is one wherein the enzyme is uniformly distributed throughout an inert material instead of being concentrated on its surface. Also U.S. Pat. No. 4,016,040 and U.S. Pat. No. 4,713,245 are documents relating to this technique Mixer granulation products, includes products where an enzyme-containing liquid is added to a dry powder composition of conventional granulating components. The liquid and the powder in a suitable proportion are mixed and as the moisture of the liquid is absorbed in the dry powder, the components of the dry powder will start to adhere and agglomerate and particles will build up, forming granulates comprising the enzyme. Such a process is described in U.S. Pat. No. 4,106,991 (NOVO NORDISK) and related documents EP 170360 B1 (NOVO NORDISK), EP 304332 B1 (NOVO NORDISK), EP 304331 (NOVO NORDISK), WO 90/09440 (NOVO NORDISK) and WO 90/09428 (NOVO NORDISK). In a particular product of this process wherein various high-shear mixers can be used as granulators, granulates consisting of the enzyme, fillers and binders etc. are mixed with cellulose fibres to reinforce the particles to give the so-called T-granulate. Reinforced particles, being more robust, release less enzymatic dust.

Methods for preparing a visco-elastic liquid core particle include those described in WO 02/28991 and is hereby incorporated by reference.

In a particular embodiment of the present invention the synthetic polymer and/or the poly-saccharide and/or the protein source and or the antioxidants are mixed together with a liquid e.g. enzyme concentrate or fermentation broth and then atomised onto preformed cores in a coating chamber e.g. a fluid bed, a multistage fluid bed, a fluid bed spray drier optionally with recirculation of fine particles.

Preparation of the Salt Coating

The salt coating may be applied onto the granule comprising the matrix comprising the active compound by atomization onto the granules in a fluid bed or a fluid bed spray dryer, the salt-coating may further be applied in vacuum mixers, dragee type coaters (pan-drum coaters), equipment for coating of seeds, equipment comprising rotating bottoms (eks. Roto Glatt, CF granulators (Freund), torbed processors (Gauda) or in rotating fluid bed processors such as Omnitex (Nara).

After applying the salt layer the granule may optionally be dried. The drying of the salt coated granule can be achieved by any drying method available to the skilled person, such as spray-drying, freeze drying, vacuum drying, fluid bed drying, pan drum coating and microwave drying. Drying of the salt coated granule can also be combined with granulation methods which comprise e.g. the use of a fluid bed, a fluid bed spray dryer (FSD) or a Multi-stage dryer (MSD).

Preparation of Additional Coating

Conventional coatings and methods as known to the art may suitably be used, such as the coatings described in Danish PA 2002 00473, WO 89/08694, WO 89/08695, 270 608 B1 and/or WO 00/01793. Other examples of conventional coating materials may be found in U.S. Pat. No. 4,106,991, EP 170360, EP 304332, EP 304331, EP 458849, EP 458845, WO 97/39116, WO 92/12645A, WO 89/08695, WO 89/08694, WO 87/07292, WO 91/06638, WO 92/13030, WO 93/07260, WO 93/07263, WO 96/38527, WO 96/16151, WO 97/23606, WO 01/25412, WO 02/20746, WO 02/28369, U.S. Pat. No. 5,879,920, U.S. Pat. No. 5,324,649, U.S. Pat. No. 4,689,297, U.S. Pat. No. 6,348,442, EP 206417, EP 193829, DE 4344215, DE 4322229 A, DE 263790, JP 61162185 A and/or JP 58179492.

The coating may be prepared by the same methods as mentioned above in the section "Preparation of the core matrix" and "Preparation of the salt coating".

Compositions Comprising the Coated Particle and Their Application

The invention also relates to compositions comprising the granules of the invention. The composition may be any composition, but particularly the compositions which are well suited are cleaning compositions, textile processing compositions, leather processing compositions, pulp or paper processing compositions, food and beverage compositions, animal feed compositions, pharmaceutical compositions and personal care compositions.

Cleaning compositions includes detergents and anti-microbial compositions. Textile processing compositions includes compositions for enzymatic bleach and/or stone washing of textiles, such as denim. Food and beverage compositions includes enzymatic compositions used in industries producing wine, oils and fats, citrus and juice products, starch and sugar products, alcohols and/or brewed products, soy products and baking flour or dough.

The present invention also encompasses the use for treatment of textile, leather, pulp, paper, food, beverage, hard surfaces and the human or animal body. The granules may also be used in the manufacture of a medicament for treatment of the human or animal body.

Detergents

The coated particles of the invention may be added to and thus become a component of a detergent composition.

The detergent composition of the invention may for example be formulated as laundry detergent composition for hand or machine washings including a cleaning additive composition suitable for pre-treatment of stained fabrics or a fabric softener composition, or a detergent composition for use in general household hard surface cleaning operations, or a composition for hand or machine dishwashing operations.

In a specific aspect, the invention provides a detergent additive comprising the coated particles of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bo-vine origin) and the Fusarium protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include EVERLASE☐ OVOZYME☐ SAVOZYME☐ ALCALASE☐, SAVINASE☐, PRIMASE☐, DURALASE☐, ESPERASE☐, AND KANNASE☐ (Novozymes A/S), MAXATASE□, MAXACAL□, MAXAPEM□, PROPERASE□, PURAFECT□, PURAFECT OXP□, FN2□, and FN3□ FN4□ (Genencor International Inc.).

Lipases: Suitable lipases include those of bacterial or fungal origin. Chemically modified or protein engineered mutants are included. Examples of useful lipases include lipases from Humicola (synonym Thermomyces), e.g. from *H. lanuginosa* (*T. lanuginosus*) as described in EP 258 068 and EP 305 216 or from *H. insolens* as described in WO 96/13580, a *Pseudomonas lipase*, e.g. from *P. alcaligenes* or *P. pseudoalcaligenes* (EP 218 272), *P. cepacia* (EP 331 376), *P. stutzeri* (GB 1,372,034), *P. fluorescens*, Pseudomonas sp. strain SD 705 (WO 95/06720 and WO 96/27002), *P. wisconsinensis* (WO 96/12012), a *Bacillus lipase*, e.g. from *B. subtilis* (Dartois et al. (1993), Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include LIPOLASE□ and LIPOLASE ULTRA□ (Novozymes A/S).

Amylases: Suitable amylases (□ and/or □) include those of bacterial or fungal origin. Chemically modified or protein engineered mutants are included. Amylases include, for example, □-amylases obtained from Bacillus, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are DURAMYL□, TERMAMYL□, FUNGAMYL□ and BAN□ (Novozymes A/S), RAPIDASE□PURASTAR□ and PURASTAR OXAM□ (from Genencor International Inc.).

Cellulases: Suitable cellulases include those of bacterial or fungal origin. Chemically modified or protein engineered mutants are included. Suitable cellulases include cellulases from the genera Bacillus, Pseudomonas, Humicola, Fusarium, Thielavia, Acremonium, e.g. the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include CELLUZYME□, and CAREZYME□ (Novozymes A/S), CLAZINASE□, and PURADAX HA□ (Genencor International Inc.), and KAC-500(B) □ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from Coprinus, e.g. from *C. cinereus*, and variants thereof as those described in WO 93/24618, WO 95/10602, and WO 98/15257.

Commercially available peroxidases include GUARDZYME□ (Novozymes A/S).

Mannanase: Suitable mannanases include MANNAWAY□(Novozymes A/S).

The detergent enzyme(s) may be included in a detergent composition by adding separate additives containing one or more enzymes, or by adding a combined additive comprising all of these enzymes. A detergent additive of the invention, i.e. a separate additive or a combined addiyive, may be formulated so as to contain one or more of the particles of the invention comprising different enzymes.

The detergent composition of the invention may be in any convenient dry form, e.g., a bar, a tablet, a powder, a granule or a paste. It may also be a liquid detergent, in particular non-aqueous liquid detergent.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system, which may comprise a $H_2O_2$ source such as perborate or percarbonate, which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

The enzyme of the invention may additionally be incorporated in the detergent formulations disclosed in WO 97/07202, which is hereby incorporated as reference.

EXAMPLES

Example 1

Uncoated protease granulates (SAVINASE□) were produced by:

A powder composition prepared from the following (all percentages given as % of dry granulate):

10% Fibrous cellulose (Arbocel BC 200)

8% Kaolin

5% Dextrin (Avedex)

Stabilizer components as given in the examples

Finely ground sodium sulfate ad 100% was mixed in a Lödige mixer and sprayed with protease (SAVINASE□ ultrafiltrate wherein 5% sugar and stabilizers as given in the examples were dissolved. The moist mixture was exposed to a compacting and granulating influence as described in example 1 of U.S. Pat. No. 4,106,991. The granulate was subsequently dried in a fluid bed.

The stability of the enzyme granulates in different powder detergents and at different conditions was measured by adding 2% of the produced granulates to the detergent and storing the samples in climate chambers in open beakers.

Stability Sesign:

I: 4 weeks at 35° C./55% RH (low humidity) bleach containing powder detergent

II: 2 weeks at 37° C./70% RH (high humidity) bleach containing powder detergent

III: 4 weeks at 37° C./70% RH (high humidity) non-bleach powder detergent:

| Added components | | | % Residual activity | | |
|---|---|---|---|---|---|
| Sodium thio-sulfate % | Rice starch % | PVP % | I | II | III |
| 1 | 10 | 0 | 43.4 | 14.5 | 72.9 |
| 1 | 10 | 2 | 45.8 | 29.9 | 95.0 |

This example illustrates how PVP increases the stability in high humidity environments.

Example 2

Granules were prepared as in example 1.

| Added components | | | % Residual activity | | |
|---|---|---|---|---|---|
| Sodium thio-sulfate % | Rice starch % | PVP % | I | II | III |
| 0 | 5 | 1 | 37.7 | 21.0 | 80.6 |
| 2 | 5 | 1 | 53.3 | 23.1 | 93.0 |

This example illustrates how sodium thiosulfate increases the stability in low humidity and in bleach containing environments.

Example 3

Granules were prepared as in example 1.

| Added components | | | % Residual activity | | |
|---|---|---|---|---|---|
| Sodium thio-sulfate % | Rice starch % | PVP % | I | II | III |
| 2 | 0 | 1 | 52.7 | 24.1 | 89.6 |
| 2 | 10 | 1 | 60.4 | 29.4 | 93.1 |

This example illustrates how a polysaccharide such as rice starch increases the stability in high and low humidity environments and in bleach containing and none bleach environments.

Example 4

Granules were prepared as described in example 1 and subsequently coated in a fluid bed with 5% sodium sulfate (by spraying an aqueous liquid composed by 28% sodium sulfate, 1% dextrin and 4% titan dioxide onto the granulates). The granulates were further coated with wax as given in WO 97/39116 example 18. Finally the granules were fluid bed coated with 3% Sepifilm (by spraying an aqueous solution of 15% Sepifilm LP030 from Seppic onto the granulates).

Stability Design:

IV: 8 weeks at 35° C./55% RH (low humidity) bleach containing powder detergent

V: 2 weeks at 37° C./70% RH (high humidity) bleach powder detergent:

VI: 12 weeks at 37° C./70% RH (high humidity) non-bleach containing powder detergent

| Added components | | | | | % Residual activity | | |
|---|---|---|---|---|---|---|---|
| Sodium thio-sulfate % | Potato protein % | Rice starch % | PVP % | 5% Salt coating | IV | V | VI |
| 2 | 5 | 5 | 1 | No | 61 | 30 | 61 |
| 2 | 5 | 5 | 1 | Yes | 79 | 46 | 75 |

This example illustrates that an additional even thin salt coating improve the stability in general.

Example 5

Granules were prepared as described in example 1, but also using finely ground $MgSO_4 \cdot 7H_2O$ as filler instead of sodium sulfate, and subsequently coated in a fluid bed with 5% sodium sulfate (by spraying an aqueous liquid composed by 28% sodium sulfate, 1% dextrin and 4% titan dioxide onto the granulates). The granulates were further coated with wax as given in WO 97/39116 example 18. Finally the granules were fluid bed coated with 3% Sepifilm (by spraying an aqueous solution of 15% Sepifilm LP030 from Seppic onto the granulates).

| Added components | | | | | % Residual activity | | |
|---|---|---|---|---|---|---|---|
| Sodium thio-sulfate % | Potato protein % | Rice starch % | PVP % | Filler | IV | V | VI |
| 2 | 5 | 5 | 1 | $Na_2SO_4$ | 79 | 46 | 75 |
| 2 | 5 | 5 | 1 | $MgSO_4$ | 88 | 64 | 86 |

This example illustrates that $MgSO_4$ can further enhance stability in general.

Example 6

Granules were prepared as given in example 1, but also using Luviskol VA64 (A 60/40 copolymer of vinyl-pyrrolidon and vinyl acetate from BASF) as synthetic polymer.

Stability Design:

I: 4 weeks at 35° C./55% RH (low humidity) bleach containing powder detergent

II: 2 weeks at 37° C./70% RH (high humidity) bleach containing powder detergent

III: 4 weeks at 37° C./70% RH (high humidity) non-bleach powder detergent:

| Added components | | | | | % Residual activity | | |
|---|---|---|---|---|---|---|---|
| Sodium thiosulfate % | Potato protein % | Rice starch % | Synthetic polymer % | Synthetic polymer | I | II | III |
| 2 | 5 | 5 | 0 | — | 53.0 | 8.7 | 62.3 |
| 2 | 5 | 5 | 1 | PVP | 53.3 | 23.1 | 93.0 |
| 2 | 5 | 5 | 1 | VA64 | 53.6 | 18.2 | 88.0 |

This example illustrates that the VA64 copolymer also is an efficient stabilizer.

Example 7

Granules were prepared as given in example 4 (i.e. with a 5% salt coating), but without the final Sepifilm and using both rice and corn starch.

Stability Design:

VII: 12 weeks at 35° C./55% RH (low humidity) bleach containing powder detergent

| Added components | | | | % Residual activity VII |
|---|---|---|---|---|
| Sodium thio-sulfate % | PVP % | Starch % | Starch Type | |
| 2 | 1 | 10 | Rice | 73 |
| 2 | 1 | 10 | Corn | 74 |

This example illustrates that other starch types than rice can be used

Example 8

Granules were prepared as given in example 7 (i.e. with a 5% salt coating but no Sepifilm), using different enzyme types.

Stability Design:

VII: 8 weeks at 37° C./70% RH (high humidity) non-bleach powder detergent

| | Added components | | | | % Residual activity | | | |
|---|---|---|---|---|---|---|---|---|
| Enzyme Type | Sodium thio-sulfate % | Rice starch % | PVP % | 5% Salt coating | V | VI | VII | VIII |
| Savinase (protease) | 0 | 0 | 0 | No | 13 | — | 26 | 59 |
| Savinase (protease) | 2 | 10 | 1 | Yes | 28 | — | 60 | 89 |
| Amylase | 0 | 0 | 0 | No | 2 | 40 | 0 | — |
| Amylase | 2 | 10 | 1 | Yes | 8 | 73 | 47 | — |
| Lipase | 0 | 0 | 0 | No | 12 | — | 12 | 17 |
| Lipase | 2 | 10 | 1 | Yes | 23 | — | 40 | 20 |
| Cellulase | 0 | 0 | 0 | No | 7 | — | 22 | — |
| Cellulase | 2 | 10 | 1 | Yes | 7 | — | 56 | — |

This example illustrates that the stabilization system is efficient on different enzyme types.

The invention claimed is:

1. A granule comprising a core matrix and one or more coatings, wherein the core matrix comprises:
   a. an active compound;
   b. a synthetic polymer in an amount of 0.1 to 10% by weight of the core matrix;
   c. antioxidant or reducing agent in an amount of 0.2 to 5% by weight of the core matrix; and
   d. magnesium salt.

2. The granule according to claim 1, wherein the matrix further comprises a polysaccharide in an amount greater than 2% by weight of the core matrix.

3. The granule according to claim 1, wherein the synthetic polymer is present in an amount of 1 to 2% by weight of the core matrix.

4. The granule according to claim 1, wherein the antioxidant or reducing agent are present in an amount of 1 to 3% by weight of the core matrix.

5. The granule according to claim 1, wherein the active compound is an enzyme.

6. The granule according to claim 1, wherein the synthetic polymer is a polyvinyl polymer selected from the group consisting of PVP, PVA and copolymers thereof.

7. The granule according to claim 1, wherein the antioxidant or reducing agent is selected from the group of sodium thiosulfate, sodium sulfite, thiodipropionic acid, erythorbate, ascorbate or methionine.

8. The granule according to claim 1, wherein the synthetic polymer is PVP and the antioxidant is sodium thiosulfate.

9. The granule according to claim 1, wherein the core matrix further comprises a polysaccharide in an amount of 2% to 75% by weight of the core matrix.

10. The granule according to claim 2, wherein the polysaccharide is starch.

11. The granule according to claim 1, where the core matrix is coated onto a preformed core.

12. The granule of claim 5, wherein the magnesium salt comprises magnesium sulfate or hydrated magnesium sulfate.

13. The granule according to claim 12, wherein the magnesium sulfate is present in an amount of 1 to 70% by weight of the core matrix.

14. The granule according to claim 1, wherein the granule is coated with a salt layer.

15. The granule according to claim 14, wherein the salt layer contains 2% to 30% by weight of the core matrix and salt layer.

16. The granule according to claim 14, wherein the salt layer contains 3 to 10% by weight of the core matrix and the salt layer.

17. The granule according to claim 14, wherein the salt layer is 2 to 100 µ thick.

18. The granule according to claim 1, wherein the granule further comprises a protective coating.

19. A process for preparing a granule, comprising the steps of:
   a. preparing a core matrix comprising an active compound; a synthetic polymer in an amount of 0.1 to 10% by weight of the core matrix; antioxidant or reducing agent in an amount of 0.2 to 5% by weight of the core matrix; and magnesium salt; and
   b. applying one or more coating to said core matrix.

20. The process according to claim 19, where the granules are prepared in a mixer, a fluid bed, a fluid bed spray dryer, a spray dryer or an extruder.

21. A granule comprising a core matrix and one or more coatings, wherein the core matrix comprises:
   a. an active compound;
   b. a synthetic polymer in an amount of 0.1 to 10% by weight of the core matrix; and
   c. antioxidant or reducing agent in an amount of 0.2 to 5% by weight of the core matrix, and
   d. magnesium sulfate or hydrated magnesium sulfate.

22. A granule in accordance with claim 1, wherein the magnesium salt is present in an amount of 1% to 70% by weight of the core matrix.

23. A process in accordance with claim 19, wherein the matrix further comprises a polysaccharide in an amount greater than 2% by weight of the core matrix.

24. A process in accordance with claim 19, wherein the synthetic polymer is present in an amount of 1 to 2% by weight of the core matrix.

25. A process in accordance with claim 19, wherein the antioxidant or reducing agent are present in an amount of 1 to 3% by weight of the core matrix.

26. A process in accordance with claim 19, wherein the active compound is an enzyme.

27. A process in accordance with claim 19, wherein the synthetic polymer is a polyvinyl polymer selected from the group consisting of PVP, PVA and copolymers thereof.

28. A process in accordance with claim 19, wherein the antioxidant or reducing agent is selected from the group of sodium thiosulfate, sodium sulfite, thiodipropionic acid, erythorbate, ascorbate or methionine.

29. A process in accordance with claim 19, wherein the synthetic polymer is PVP and the antioxidant is sodium thiosulfate.

30. A process in accordance with claim 19, wherein the core matrix further comprises a polysaccharide in an amount of 2% to 75% by weight of the core matrix.

31. A process in accordance with claim 19, wherein the magnesium salt is magnesium sulfate or hydrated magnesium sulfate.

32. A process in accordance with claim 19, wherein the magnesium salt is present in an amount of 1% to 70% by weight of the core matrix.

* * * * *